United States Patent [19]
Platz et al.

[11] Patent Number: 5,354,562
[45] Date of Patent: Oct. 11, 1994

[54] PROCESS FOR PREPARING MICRONIZED POLYPEPTIDE DRUGS

[75] Inventors: Robert M. Platz, Half Moon Bay; Anna Ip, Moorpark; Clyde L. Whitham, Montara, all of Calif.

[73] Assignee: SRI International, Menlo Park, Calif.

[21] Appl. No.: 17,540

[22] Filed: Feb. 16, 1993

Related U.S. Application Data

[63] Continuation-in-part of Ser. No. 823,218, Jan. 21, 1992, abandoned.

[51] Int. Cl.$^5$ ................................................ A61K 9/14
[52] U.S. Cl. ........................................ 424/489; 424/46
[58] Field of Search .......................... 424/489, 473.46; 514/808

[56] References Cited

U.S. PATENT DOCUMENTS

| | | | |
|---|---|---|---|
| 4,783,484 | 11/1988 | Violante | 514/535 |
| 4,900,734 | 2/1990 | Maxson | 514/171 |
| 4,940,588 | 7/1990 | Sparks | 424/490 |
| 5,011,678 | 4/1991 | Wang | 424/45 |
| 5,057,321 | 10/1991 | Edgren | 424/413 |

FOREIGN PATENT DOCUMENTS 0384752 8/1990 European Pat. Off. .
WO90/09781 9/1990 PCT Int'l Appl. .
WO90/09787 9/1990 PCT Int'l Appl. .
WO11091 10/1990 PCT Int'l Appl. .
WO90/11091 10/1990 PCT Int'l Appl. .
WO91/16038 10/1991 PCT Int'l Appl. .

OTHER PUBLICATIONS

Pikal, M. J., "Freeze-Drying of Proteins, Part 1: Process Design", *BioPharm* (Sep. 1990) pp. 18–27.
Franks, F., "Freeze-Drying: From Empiricism to Predictability", *Cryoletters* (1990) 11:93–110.

*Primary Examiner*—Thurman K. Page
*Assistant Examiner*—William E. Benston, Jr.
*Attorney, Agent, or Firm*—Felissa H. Cagan

[57] ABSTRACT

Solid particle aerosol formulations of polypeptide drugs are made by lyophilizing solutions of the drugs which contain milling stabilizers that inhibit degradation of the drug during subsequent milling. The lyophilized drug is milled in fluid energy mills that have been fitted with abrasion-resistant materials and which use pure nitrogen that has been filtered to eliminate particles of greater than 0.1 μm to transport the drug. The use of (a) milling stabilizers in the solution and (b) abrasion-resistant fluid energy mills that use pure filtered nitrogen in the milling step reduce insoluble contaminants and inactive fractions in the milled product.

16 Claims, No Drawings

PROCESS FOR PREPARING MICRONIZED POLYPEPTIDE DRUGS

CROSS-REFERENCE TO A RELATED APPLICATION

This application is a continuation-in-part of U.S. patent application Ser. No. 07/823,218 filed 21 January 1992, now abandoned the disclosure of which is incorporated herein by reference.

DESCRIPTION

1. Technical Field

The present invention is in the field of pharmaceutical formulation. More particularly, it concerns improvements in a process for micronizing polypeptide drugs into powders that are suitable for formulation as solid particle aerosols.

2. Background

Inhalation therapy involves the administration of a drug in an aerosol form to the respiratory tract. Two types of aerosols are employed: liquid particles and solid particles. The liquid aerosols are generated by nebulizing solutions of the drug. Solid particle aerosols are either in the form of a powder suspended in a propellant which is administered from a metered dose inhaler or simply as a powder that is administered from a dry powder inhaler. In the case of polypeptide drugs, solid particle aerosols are typically made by lyophilizing the drug from solution and then milling or grinding the lyophilized drug to the desired particle size distribution for pulmonary administration.

Prior workers have recognized certain stability problems in making such drugs. First, prior workers have recognized that removal of residual water during the lyophilization in the presence of protective agents provides a more stable lyophilized product. A variety of excipients have been proposed as such cryoprotectants (Pikal, M. J., *Biopharm,* (1990) 3(8):18–27 and Franks, F., *Cryoletters* (1990) 11:93–110.

Prior workers have also recognized and addressed problems associated with the "stability" of drug powders that are used in solid particle aerosols. These "stability" problems involve the particles being adsorbed or absorbed by materials in which they come into contact during their handling or the particles forming agglomerates. For instance, PCT Application Publication WO90/09781 suggests using "extender" molecules to avoid particle adsorption, absorption, or agglomeration while metering the particles into unit dose containers. Among the suggested extenders are amino acids (particularly Dn-methionine), mono-, di-, and polysaccharides, and polypeptides.

To the best of applicants' knowledge, the art has not recognized or addressed the deleterious effects of the grinding or milling step of the powder production on the solubility and biological activity of the product powder. In this regard, the present invention is directed to a means for reducing the amounts of insoluble material and biologically inactive material produced when a polypeptide drug is lyophilized and milled into a powder for administration as a solid particle aerosol.

DISCLOSURE OF THE INVENTION

The invention relates to improvements in a process for preparing a micronized polypeptide drug in which a solution of the drug is lyophilized and the lyophilized drug is milled to a powder in a fluid energy mill using a pressurized feed gas. One improvement comprises using a purified inert feed gas which has been filtered to remove particles greater than about 0.1 $\mu$m from the feed gas whereby water insoluble contaminants in the powder are reduced. Another improvement applies to instances where the drug is labile under the milling conditions and comprises incorporating a milling stabilizer in the polypeptide drug whereby the production of biologically inactive material in the milling step is reduced.

MODES FOR CARRYING OUT THE INVENTION

The present invention is useful for transforming polypeptide drugs into a powder form that is suitable for aerosol administration or for use in injectable suspensions. As used herein, the term "polypeptide" intends molecules composed of about 10 or more amino acids linked by peptide bonds. The polypeptides may include moieties, e.g., sugars other than amino acids, or be complexed with other moieties such as lipids. Examples of such polypeptides are insulin, interferon $\alpha$, interferon $\beta$, interferon $\gamma$, interleukin 1-7, granulocyte colony stimulating factor (GCSF), macrophage granulocyte colony stimulating factor (MGCSF), epidermal growth factor (EGF), insulin-like growth factors I and 2 (IGF-1 and 2, transforming growth factor $\alpha$ (TGF-$\alpha$), transforming growth factors $\beta$1-3 (TGF-$\beta$1, 2 and 3), tissue plasminogen activator (TPA), platelet-derived growth factor (PDGF), erythropoietin (EPO), human growth hormone (HGH), and other hormones, growth factors, and neuropeptides. These polypeptides may be prepared by isolating them from natural sources (body tissues or fluids), by synthesizing them by recombinant DNA technology, or in the case of relatively small molecules, by synthesizing them by solid-phase techniques with or without ligation.

The first step in the process for forming the polypeptides into micronized particles is lyophilization. If the polypeptide as isolated or synthesized is in solution, no solvent need be added. If it is in a dry state, the polypeptide is dissolved in an appropriate solvent. In many instances, the polypeptide is water soluble. It will be appreciated that low solubility polypeptides simply require use of a greater volume of solvent. The polypeptide is lyophilized from a frozen solution. If the polypeptide is labile to the conditions to which it is subjected during milling (i.e., shear, pressure, temperature), a milling stabilizer is added to the solution. Such stabilizers include sugars, e.g., sorbitol, mannitol, sucrose, lactose, and trehalose, surfactants such as polyvinylpyrolidone, and water-soluble proteins such as serum albumins (bovine, human, chicken, goat, etc.). The stabilizer will normally be added to the solution at concentrations of 0.5 to 50 mg/ml, preferably 1 to 20 mg/ml. Sorbitol in combination with other sugars is a preferred stabilizer. Alternatively, the stabilizer may be mixed homogeneously with the lyophilized cake. It will be appreciated that the optimum stabilizer or combination of stabilizers will vary from drug to drug and that the optimum stabilizer(s) and amount of stabilizer for a given polypeptide drug may need to be determined empirically.

The solution is lyophilized by freezing the solution and subjecting the frozen mass to a vacuum. Conventional lyophilization equipment may be used. Normally, the solution will be cooled to $-10°$ C. to $-60°$ C., preferably $-15°$ C. to $-45°$ C. and subjected to a vacuum of 50 to 750 millitorr, preferably 100 to 250 millitorr for 50 to 120 hours.

The lyophilized polypeptide is then size reduced in a grinding mill, preferably a fluid energy mill also known as a jet mill. These mills employ high velocity gas streams to carry feed particles into contact with each other and/or the surfaces of a grinding chamber. In one type the fluid energy is admitted via a multiplicity of high velocity gas streams at an angle around a portion or all of the periphery of a cylindrical milling-classifying chamber. In another type, fluid streams convey the particles at high velocity into a chamber where two streams impact upon each other. In another type the fluid stream conveys the particles against a stationary impact surface or around a toroidal channel. In all types there is a high energy release and a high order of turbulence which causes the particles to grind upon themselves and upon the mill surface and to be fractured. Most mills classify particles centrifugally using the energy of the fluid stream and have means for returning oversize particles to the grinding chamber for further size reduction. Mills that employ the angle-jets are preferred. Examples of commercial embodiments of such mills are the Micronizer (Sturtevant Mill Corp.), the Jet Pulverizer (Jet Pulverizer Co.), the Reductionizer, the Micron-Master, the Trost M. N., and the Jet-O-Mizer. Structurally these mills comprise a cylindrical grinding chamber wherein the lyophilized polypeptide drug is acted upon by a number of gas jets issuing through orifices spaced around the periphery of the chamber. The rotating gas discharges at the center of the chamber carrying the fines with it, while the coarse particles are thrown toward the chamber wall where they are subjected to further reduction by impact from particles and gas in the incoming jets. The outlet from the grinding chamber normally leads directly into a centrifugal product collector.

In order to reduce the amount of insoluble contaminants (i.e., materials that are insoluble in water at 37° C.) present in the product powder, applicants have modified the conventional milling procedure in several important respects. First, any parts of the mill (e.g., solder or weld joints) that may be subject to abrasion and degradation are replaced with materials that are more resistant to abrasion and degradation under the milling condition. Second, an inert feed gas (e.g., nitrogen) is used to fluidize the particles. In this regard, the term "inert" intends that the gas will not react with the lyophilized feed material under the milling conditions. Liquid nitrogen is a preferred source of inert gas because it is ultrapure and it helps cool the mill and the product. Third, the incoming feed gas is filtered prior to introduction into the mill to eliminate contaminants of less than about 0.1 μm particle size. Filtration may be accomplished by placing commercially available ULPA (ultrahigh efficiency) filters (e.g., Wafergard, Millipore, Inc.) in the incoming gas lines. Use of high purity gas lines is desirable to avoid introducing contaminants into the polypeptide.

As indicated above, applicants further employ milling stabilizers to reduce shear, pressure and/or temperature degradation of the polypeptide drug. These stabilizers my also protect the polypeptide from degradation during the lyophilization and/or during storage.

The particle size of the milled powder is primarily dependent upon the energy imparted by the gas to the particles which in turn is related to the pressure of the feed gas. This pressure will normally range between about 10 to 120 psig, more usually 80 to 110 psig. In general, lower pressures in this range (i.e., 10 to 30 psig) will produce larger particles (i.e., 4 to 15 μm in diameter) whereas higher pressures will produce smaller particles (i.e., 0.5 to 4 μm in diameter).

The desired particle size for a given polypeptide drug will depend upon the site in the respiratory tract for which the drug is targeted. Generally, particles below about 4 μm in diameter (usually 0.5 to 4 μm) will deposit in the therapeutically effective lower pulmonary regions when administered as an aerosol into the respiratory tract whereas larger particles (4 to 10 μm) will lodge in the upper airways of the respiratory tract. It will be appreciated that the particle sizes recited herein refer to at a mass distribution of particles defined by the mass median diameter (where 50% of the mass of the particles is above the stated size and 50% of the mass is below the stated size). Particle sizes my be determined by commercially available particle size analyzers.

By using the improved process of the invention, insoluble contaminants in the powder product are reduced to below about 5% by weight, more usually below about 2% by weight. These contaminants have been found to increase degradation of the active ingredient in the milled powder product. In the case of polypeptides that are otherwise degraded by jet milling, the invention reduces the extent of degradation such that the polypeptide drug component of the milled powder constitutes at least about 85% active drug, preferably at least about 95% active drug.

The milled powder may be formulated with a propellant for administration via metered dose inhaler devices. The propellant will normally be a hydrocarbon or halohydrocarbon such as tetrafluoroethane, trichlorofluoromethane, dichlorofluoromethane, and the like. Surfactants may be added to the formulation to facilitate and stabilize the suspension and dispersion of the powder in the propellant and to lubricate inhaler components. The drug powder will normally constitute about 0.1 to 10% by weight of the formulation, more usually 0.5 to 2.5% by weight.

The milled powder may be formulated with bulking agents or administered neat from powder inhaler devices. When bulking agents are used, they will normally constitute about 50% to 99.9% of the formulation.

The solid particle aerosol of the polypeptide drug will be administered in one or more unit doses to provide therapeutic levels of the drug. The amount of polypeptide administered and the dosing regimen will depend upon the particular drug being administered, the indication being treated, and the patient. Accordingly, it will be appreciated that the specific amount and regimen used in given instances may vary widely.

The following examples further illustrate the invention. These examples are not intended to limit the invention in any manner.

EXAMPLE 1

Micronization of Human Growth Hormone

Lyophilization

Lyophilized recombinant human growth hormone was obtained from the manufacturer of same.

Milling

A Sturtevant Micron-Master mill (model 2") was used. Originally the feed gas to the mill was fed in at 100 psig. The insoluble fraction in the milled product was determined by U.V. spectrophotometer. In initial runs approximately 40% by weight of the milled product was insoluble.

The insoluble fraction was reduced to 20% by weight by (1) replacing the silver soldered joints in the mill with welded joints and (2) replacing the soldered copper gas lines with flexible stainless steel hose. The insoluble fraction was further reduced to 5 to 15% by weight by (1) replacing the Sturtevant gas manifold with a manifold made of electropolished stainless steel tubing and VCR couplings, (2) installing a Balston particle filter (type BK tested for removing 0.1 μm particles at 99.99% efficiency), and (3) milling with 99.99% pure nitrogen. Further reduction of insoluble material was achieved by altering the powder-feed mechanism to prevent it from drawing contaminated room air and by supplying the gas from liquid nitrogen dewar containers. The insoluble fraction was further reduced to 2.5 to 7.5% by weight by replacing the gas manifold with a high purity gas manifold and ultra high purity filters (Wafergard, Millipore, Inc.).

EXAMPLE 2

Micronization of IFN-$\beta$

Lyophilization

Aqueous solutions of IFN-$\beta$ having the following compositions were prepared.

| Component | Solution A | Solution B | Solution C |
| --- | --- | --- | --- |
| IFN/$\beta$ | 15 μg/mL | 15 μg/mL | 65 μg/mL |
| Human Serum Albumin | 1.5 mg/mL | 15 mg/mL | 1.445 mg/mL |
| NaCl | 0.6 mg/mL | 0.6 mg/mL | 0.584 mg/mL |
| Sorbitol | — | 4.5 mg/mL | — |

The solutions were lyophilized in a freeze dryer (Model No. GT4, Leybold, Cologne, Germany)

Milling

The jet mill described in Example 1 that provided the best reduction of insolubles was used. The filter on the feed gas line was obtained from Millipore Corp. (Bedford, Mass.).

The mill was operated at 80–100 psig according to manufacturer's instructions to provide a powder having greater than 50% of the particles less than 3 μm in diameter and 90% of the particles less than 5 μm in diameter.

The lyophilized powder (before micronization) and the micronized powders were assayed for IFN-$\beta$ activity using an enzyme immunoassay (EIA) (Yamazaki et al., J. Immunoassay (1989) 10:57). The results were as follows:

| Solution | Activity Before Micronization | Activity After Micronization |
| --- | --- | --- |
| A | 107 ± 17% | 65 ± 4.8% |
| B | 110 ± 25% | 102 ± 3.8% |
| C | 10.4 ± 2.5% | 8.2 ± 1.9% |

As shown, the formulation that contained both human serum albumin and sorbitol withstood the milling without significant loss of activity.

EXAMPLE 3

Micronization of GCSF

Aqueous formulations of GCSF at 1 mg/mL, glycine HCl at 1.1 mg/mL, and mannitol, lactose or sucrose at 10 mg/mL were made, lyophilized and milled. Pure nitrogen, milling pressure 100 psig, was used with a feed rate of the lyophilized material of 0.5 g/min. The milling apparatus was that used in Example 2 above. The milled powders contained insignificant amounts of insoluble material but significant amounts of soluble aggregates.

In an attempt to eliminate soluble aggregates, an aqueous formulation of GCSF at 1.0 mg/mL, mannitol at 9.0 mg/mL and sorbitol at 1.0 mg/mL was made, lyophilized and milled as above. The addition of sorbitol reduced the level of soluble aggregates in the milled powder to 4% ± 1.87. Samples of unmilled powder and milled powder of this formulation were reconstituted in glycine-buffered water (pH 3.5) and analyzed by size-exclusion HP chromatography. The resulting chromatographs indicated there was insignificant degradation of the powder by the milling.

EXAMPLE 4

Evaluation of the Milling Process

Lyophilized recombinant human growth hormone was obtained from the manufacturer of same.

To evaluate the milling process, the initial system tested comprised a Sturtevant Micron-Master mill (model 2") with a copper piping system. 99.99% pure compressed nitrogen was used as a feed gas. In order to evaluate the amount of insoluble (inactive) protein, the milled protein was dissolved in phosphate buffer, filtered through a 0.2 μm filter, and the resulting solution was analyzed by UV spectroscopy. The results were compared with un-milled protein. Following the milling process, there was 39–43% insoluble protein in the product.

In order to reduce the amount of insoluble proteins, the copper piping system was replaced with flexible stainless steel hose and the silver soldered joints of the original mill were replaced with welded joints. Following the milling process under these conditions, the powdered product comprised 10–20% insoluble protein as analyzed above.

Further reduction of the insoluble protein was accomplished by replacing the stainless steel gas manifold with electropolished stainless steel tubing and VCR couplings. In addition, a Balston particle filter (type BK tested for removing 0.1 μm particles at 99.99% efficiency) was installed in the feed gas system. Following the milling process under these conditions, the powdered product comprised 4–14% insoluble protein.

In a final process, a high-purity manifold system was designed to replace the manifold made of electropolished stainless steel tubing and VCR couplings. The ultrapure feed gas was supplied from two liquid nitrogen dewars. Further, the powder feed system mechanism was altered to prevent drawing contaminated room air into the system. The feed funnel of the jet mill was adapted to fit a glass powder funnel with a "TEFLON" screw feeder. Filtered nitrogen gas was maintained in the funnel during the milling operation. Following the milling process under these conditions, the powdered product comprised only 0.5–1.7% insoluble protein.

Modifications of the above-described modes for carrying out the invention that are obvious to those of skill in the field of pharmaceutical formulation and related fields are intended to be within the scope of the following claims.

We claim:

1. In a process for preparing a micronized polypeptide drug comprising lyophilizing a solution of the drug in a solvent and milling the lyophilized drug in a fluid energy mill using a pressurized gas to form a powder, the improvement comprising using a pure inert gas filtered to remove particles greater than about 0.1 $\mu$m and the improvement wherein the parts of the mill that are contacted by the pressurized gas in which the polypeptide drug is being carried are not substantially abraded by said drug-carrying gas whereby the insoluble contaminants in the micronized polypeptide drug comprise less than 2% by weight of the polypeptide drug.

2. The process of claim i wherein the polypeptide drug is labile under the milling conditions and the lyophilized drug contains a milling stabilizer.

3. The process of claim 2 wherein the milling stabilizer comprises sorbitol, mannitol, sucrose, lactose, trehalose, serum albumin, polyvinylpyrrolidone, or mixtures thereof.

4. The process of claim 1 wherein the pressure of the nitrogen is in the range of 10 to 120 psig.

5. The process of claim 4 wherein the source of the nitrogen is liquid nitrogen.

6. The process of claim 1 wherein the particle size of the micronized polypeptide drug is in the range of about 0.5 to about 15 $\mu$m.

7. The process of claim 1 wherein the solvent is water.

8. The process of claim 1 wherein the micronized polypeptide drug is suitable for administration as a solid particle aerosol.

9. In a process for preparing a micronized polypeptide drug comprising lyophilizing a solution of the drug in a solvent and milling the lyophilized drug in a fluid energy mill using a pressurized gas to form a powder, the improvement comprising using a pure inert gas filtered to remove particles greater than about 0.1 $\mu$m and the improvement wherein the parts of the mill that are contacted by the pressurized gas in which the polypeptide drug is being carried are not substantially abraded by said drug-carrying gas whereby at least 85% of the polypeptide drug is in active form.

10. The process of claim 9 wherein the polypeptide drug is labile under the milling conditions and the lyophilized drug contains a milling stabilizer.

11. The process of claim 10 wherein the milling stabilizer comprises sorbitol, mannitol, sucrose, lactose, trehalose, serum albumin, polyvinylpyrrolidone or mixtures thereof.

12. The process of claim 9 wherein the pressure of the nitrogen is in the range of 10 to 120 psig.

13. The process of claim 9 wherein the pressurized gas is nitrogen and the source of the nitrogen is liquid nitrogen.

14. The process of claim 9 wherein the particle size of the micronized polypeptide drug is in the range of about 0.5 to about 15 $\mu$m.

15. The process of claim 9 wherein the solvent is water.

16. The process of claim 9 wherein the micronized polypeptide drug is suitable for administration as a solid particle aerosol.

* * * * *